United States Patent
Kunsmann-Keitel et al.

(10) Patent No.: US 6,822,110 B2
(45) Date of Patent: Nov. 23, 2004

(54) CAO-CATALYZED PREPARATION OF ISOPHORONENITRILE

(75) Inventors: Dagmar Pascale Kunsmann-Keitel, Limburgerhof (DE); Gerold Braun, Ludwigshafen (DE); Ingo Münster, Böhl-Iggelheim (DE); Klaus Mundinger, Limburgerhof (DE); Gunter Scherhag, Heidelberg (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/701,513

(22) Filed: Nov. 6, 2003

(65) Prior Publication Data

US 2004/0092761 A1 May 13, 2004

(30) Foreign Application Priority Data

Nov. 7, 2002 (DE) .......................................... 102 51 680

(51) Int. Cl.$^7$ ........................................... C07C 253/00
(52) U.S. Cl. ...................................................... 558/315
(58) Field of Search ......................................... 558/315

(56) References Cited

U.S. PATENT DOCUMENTS

| 5,183,915 A | 2/1993 | Forguy et al. |
| 5,235,089 A | 8/1993 | Woodbury et al. |
| 5,254,711 A | 10/1993 | Pander et al. |
| 6,022,988 A | 2/2000 | Fischer et al. |

FOREIGN PATENT DOCUMENTS

| CA | 2150931 | 10/1998 |
| EP | 1 085 871 | 7/1960 |
| EP | 1 240 854 | 5/1967 |
| EP | 0 433 615 | 6/1991 |
| EP | 0 554 786 | 8/1993 |
| EP | 0 671 384 | 9/1995 |
| EP | 0 985 659 | 3/2000 |
| GB | 887 411 | 1/1962 |
| GB | 887 412 | 1/1962 |
| GB | 887 413 | 1/1962 |
| GB | 1 047 920 | 11/1966 |

OTHER PUBLICATIONS

Derwent ABST. 91–254225/35.

Primary Examiner—Taofiq Solola
Assistant Examiner—Robin Waller
(74) Attorney, Agent, or Firm—Keil & Weinkauf

(57) ABSTRACT

The present invention describes a process for preparing isophoronenitrile by adding HCN to isophorone. The catalyst used is CaO which has a BET surface area of >1.5 m$^2$/g. The use of such a catalyst achieves high yields and selectivities.

10 Claims, No Drawings

CAO-CATALYZED PREPARATION OF ISOPHORONENITRILE

The present invention relates to a process for preparing isophoronenitrile by adding HCN to isophorone and using CaO as a catalyst.

The addition of HCN to isophorone is a reaction known per se. This is illustrated in the following equation (I).

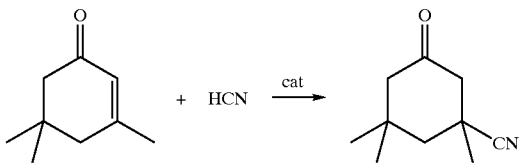

The reaction proceeds in the presence of a catalyst whose properties are critical for a successful execution of the addition reaction. The task of the catalyst is to form cyanide ions from the HCN in an amount at which the desired addition proceeds in high yield and selectivity. The catalyst has to immediately react the added amount of HCN with the isophorone. This amount must not be too low, since long reaction times would otherwise be necessary to achieve an acceptable yield. In addition, when the reaction time is too long and the cyanide ion concentration too low, decomposition of the isophoronenitrile formed to isophorone and HCN occurs. When there is too high a steady state concentration of HCN, which may of course also result from too rapid dropwise addition or the presence of an unsuitable catalyst, polymerization of HCN occurs which is therefore lost to the further reaction. A further undesired side reaction is the dimerization of isophorone to diisophorone in the presence of bases. The diisophorone can then, especially at high reaction temperatures and relatively long reaction time, polymerize and be lost as starting material.

The catalysts which are used are generally bases which form cyanide ions with the HCN under reaction conditions.

The prior art discloses the use of various bases.

DE-B 1 085 871 describes a process for adding HCN to cyclic ketones, including isophorone. The catalysts used in the addition are strongly alkaline catalysts which form cyanide ions. These are alkali metals and their carbonates, alkaline earth metals and alkali metal and alkaline earth metal alkoxides, oxides, hydroxides, peroxides and cyanides, tertiary amines and quaternary ammonium bases. Typical examples of catalysts which may be used include sodium, potassium, lithium, sodium methoxide, potassium butoxide, lithium ethoxide, magnesium ethoxide, sodium oxide, potassium hydroxide, calcium oxide, barium hydroxide, strontium hydroxide, sodium peroxide, magnesium peroxide, potassium cyanide, lithium cyanide, barium cyanide, magnesium cyanide, sodium carbonate, potassium carbonate, trimethylamine, triethylamine, triethanolamine, octyldimethylamine, N-methylmorpholine, benzyltrimethylammonium hydroxide, dibenzyldimethylammonium hydroxide and dodecenyltriethylammonium hydroxide.

DE-B 1 240 854 discloses a process for preparing isophoronenitrile by adding HCN to isophorone, in which an alkaline catalyst is used in amounts of $<10^{-1}$ to $10^{-3}\%$ by weight and operation is effected in the absence of a solvent. Alkali metal cyanides, hydroxides and alkoxides are specified as particularly suitable catalysts, and the examples describe the use of NaOH and sodium methoxide.

EP-A 0 443 615 discloses carrying out the addition of HCN to isophorone using LiOH as a catalyst, which is said to achieve advantageous results.

The catalyst used in the process described in U.S. Pat No. 5,183,915 for adding HCN to isophorone is an onium salt of nitrogen, phosphorus or arsenic with cyanide as the counterion.

Catalysts which can be used in the reaction disclosed in U.S. Pat. No. 5,235,089 for preparing isophoronenitrile by adding HCN to isophorone are catalysts selected from the group consisting of lithium hydroxide, lithium hydroxide monohydrate, lithium cyanide or solutions thereof.

According to EP-A 0 554 786, the base-catalyzed reaction of isophorone with HCN is carried out in two separate reaction zones, one reaction zone having substantially complete backmixing and the other having substantially no backmixing. Useful basic catalysts are all substances which form cyanide ions from HCN under the reaction conditions, for example hydroxides, cyanides and alkoxides of alkali metals and alkaline earth metals, and quaternary ammonium compounds. Preference is given to using alkali metal $C_1$–$C_4$-alkoxides such as sodium methoxide, sodium ethoxide, potassium methoxide, potassium tert-butoxide or lithium methoxide.

EP-A 0 671 384 discloses the use of certain organic ammonium catalysts in the reaction of HCN with isophorone to give isophoronenitrile.

Finally, in accordance with the teaching of EP-A 0 985 659, the base used in the addition of HCN to isophorone is the betaine 1,3-dimethylimidazolium-4-carboxylate.

However, there is still a need for catalysts for the addition of HCN to isophorone which are inexpensive and provide high yields and also selectivities.

It is an object of the present invention to provide such a catalyst.

We have found that this object is achieved by the use of CaO having a BET surface area of $>1.5$ $m^2/g$ in the addition of HCN to isophorone to achieve such high selectivities and yields. This provides a further catalyst for the reaction mentioned.

The catalyst which also finds use in the building industry can be obtained inexpensively in large amounts. It has also been found that the CaO used has a high activity. In general, the achievable space-time yields are higher than in the case of catalysts which are approximately comparable in price, such as LiOH, NaOH and also NaOMe. The activity is often even above that of the more complex and expensive catalysts which are mentioned in the above-cited documents. Finally, the selectivities which can be achieved are also high at from about 98 to 99% with regards to HCN and from 98 to 99% with regards to isophorone.

In order to be suitable for use in the addition of HCN to isophorone, the CaO used in particular has to have a high BET (Brunauer Emett Teller) surface area of $>1.5$ $m^2/g$. Even better results are obtained when a CaO having a BET surface area of $>2.0$ $m^2/g$, in particular $>2.3$ $m^2/g$, is used.

It has also proven advantageous when the CaO used only has a low content of impurities. The CaO should have a purity of $>96\%$, preferably $>97\%$, in particular $>98\%$.

The process according to the invention is carried out at a temperature of from 100 to 200° C., preferably from 140 to 190° C., in particular from 150 to 170° C., and atmospheric or at elevated pressure. Preference is given to carrying out the reaction at a pressure of from 1 to 10 bar, in particular from 1 to 3 bar. The amount of CaO used is from 2000 to 10000 ppm, preferably from 3000 to 6000 ppm, based on the total amount of the reactants. Suitable qualities of CaO are obtainable, for example, from Honeywell under the specification E529 (BET surface area 2.7 $m^2/g$) and Schäferkalk under the specification PRECAL 30 S (BET surface area 2.4 $m^2/g$).

Since, as already mentioned, the HCN must not be added in such a way that there is an amount (which is not converted to cyanide ions and does not directly add to isophorone) sufficient for polymerization in the reaction mixture, the rate of metered addition of HCN to isophorone selected must not be too high.

Owing to the necessary, low HCN concentrations, the initial charging of HCN with subsequent addition of isophorone is not viable. Therefore, at least a portion of the isophorone is always initially charged and the HCN is added at a temperature at which the addition to isophorone occurs at the desired rate. The catalyst also has to be present. HCN must also not be added too slowly, since, especially at high reaction temperatures, isophoronenitrile decomposes to reform HCN and isophorone.

Generally, the process according to the invention is carried out in such a way that an excess of isophorone is used, since this achieves a higher selectivity for isophoronenitrile. In general, the molar isophorone/HCN ratio is >1. For a favorable space-time yield, the isophorone excess should be kept as small as possible. Preferably, values of from 1.2 to 2, in particular from 1.3 to 1.5, should be maintained. The entire amount of isophorone can be initially charged and brought to the desired reaction temperature, before the HCN is added in the presence of the catalyst. It has proven favorable to initially charge a portion of the isophorone and, after heating to reaction temperature, to add a mixture of isophorone and HCN in a suitable ratio in the presence of the catalyst until the reaction is over. This ratio is preferably approx. 1:2. The catalyst may already be present during the heating of the isophorone. In contrast to the customary catalysts used according to the prior art, especially alkali metal salts, there is only insignificant polymerization of isophorone, if any. However, preference is given to heating a portion of the isophorone to the reaction temperature and adding the CaO afterwards. This allows any polymerization of isophorone to be further suppressed. Optionally, a small amount of the isophorone/HCN mixture is added in this procedure together with the catalyst.

Depending on the embodiment selected, HCN or an isophorone/HCN mixture is then added to the isophorone/CaO mixture having the desired reaction temperature.

Within the above-specified reaction parameters, the HCN or the isophorone/HCN mixture is metered in at such a rate that a sufficiently low steady state concentration of HCN results and a high selectivity and also a high conversion to isophoronenitrile are achieved. Only a small amount of polymerization of HCN may occur, since this would reduce the conversion and the selectivity. The exact conditions which have to be observed can be determined by those skilled in the art by routine experiments. Preference is given to determining the steady state concentrations of unconverted, free HCN and the total concentration of cyanide ions (sum of free HCN and cyanide bound as cyanohydrins of isophorone and isophoronenitrile) and adapting the reaction conditions until the values lie within the desired range. The concentrations specified are preferably determined by the Volhard and Liebig determinations respectively.

The process can be carried out batchwise, continuously or semicontinuously, although preference is given to the semicontinuous embodiment.

The process can be carried out with or without addition of a suitable solvent. Preference is given to carrying out the reaction without solvent. In the case that a solvent is used, suitable solvents are toluene and/or dimethylformamide (DMF), preferably DMF.

After the end of the reaction, the reaction mixture is worked up in a customary manner known to those skilled in the art. Excess isophorone is preferably removed by distillation and advantageously reused. Afterwards, the isophoronenitrile formed is separated from high boilers and catalyst used, preferably likewise distillatively.

The invention is now illustrated in the examples which follow, in which STY means space-time yield, IP means isophorone and IPN means isophoronenitrile.

EXAMPLES

Example 1

Isophorone (622 g, 4.5 mol) is initially charged in a stirred tank and heated to 150° C. When the reaction temperature is reached, CaO (Honeywell E529; 4.14 g; 4500 ppm, based on the total mixture) is added and the metered addition of an isophorone/HCN mixture (81 g of HCN, 3 mol; 207.3 g of IP, 1.5 mol) is commenced. After 60 minutes, the mixture has been metered in and the reaction mixture is maintained at reaction temperature for another hour. The HCN conversion is 99.5%. To determine the yield and the selectivity, the reaction mixture is fractionally distilled at 0.1 mbar. Yield of IPN based on HCN: 98.7%; selectivity based on IP: 97.1%.

Example 2 (Comparative Example)

Isophorone (865.2 g, 6.27 mol) is initially charged in a stirred tank and heated to 150° C. When the reaction temperature is reached, 20% NaOH (5.75 g, 0.34 mol % based on IP) is added and the metered addition of an isophorone/HCN mixture (113.0 g of HCN, 4.18 mol; 288.5 g of IP, 2.09 mol) is commenced. After 300 minutes, the mixture has been metered in and the reaction is maintained at reaction temperature for another hour. The HCN conversion is 100%. To determine the yield and the selectivity, the reaction mixture is fractionally distilled at 0.1 mbar. Yield of IPN based on HCN: 94.1%; selectivity based on IP: 96.3%.

Example 3 (Comparative Example)

Isophorone (865.2 g, 6.27 mol) is initially charged in a stirred tank and heated to 150° C. When the reaction temperature is reached, LiOH (0.98 g, 0.48 mol % based on IP) is added and the metered addition of the isophorone/HCN mixture (113.0 g of HCN, 4.18 mol; 288.5 g of IP, 2.09 mol) is commenced. After 300 minutes, the mixture has been metered in and the reaction is maintained at reaction temperature for a further 2.7 hours. The HCN conversion is 99.5%.

To determine the yield and the selectivity, the reaction mixture is fractionally distilled at 0.1 mbar. Yield of IPN based on HCN: 80.5%; selectivity based on IP: 95.4%.

As examples 1 to 3 show, the best selectivities and yields are achieved using CaO. The longer metering times in the case of NaOH and LiOH additionally point to a lower activity of the catalyst.

Example 4

A series of experiments was carried out using CaO (Honeywell E529) as the catalyst to determine the best reaction conditions. A portion of the isophorone used in excess was initially charged, a portion metered in in a mixture with HCN. In all experiments, the same amount of feed (103.5 g of IP, 0.75 mol; 40.5 g of HCN, 1.5 mol) was used. The remaining amount of isophorone (variable) served as the initial charge.

When the reaction temperature was reached, CaO was added to the initially charged IP and the metered addition of the IP/HCN mixture over different periods was commenced. The total reaction time was 180 minutes.

The selectivities based on both starting materials were subsequently determined by gas chromatography. The results are reported in the following table 1:

TABLE 1

Reaction of isophorone with HCN under different reaction conditions

| No. | T[° C.] | Isophorone/ HCN molar ratio | Metering time [min] | CaO [ppm] | S (HCN) | S (IP) |
|---|---|---|---|---|---|---|
| 1 | 155 | 1.5 | 100 | 3750 | 99.0 | 97.7 |
| 2 | 155 | 1.33 | 120 | 3750 | 98.1 | 97.5 |
| 3 | 165 | 1.2 | 84 | 4100 | 95.9 | 99.9 |
| 4 | 165 | 1.33 | 84 | 3750 | 97.5 | 99.0 |
| 5 | 175 | 1.33 | 80 | 3750 | 97.1 | 98.2 |
| 6 | 175 | 1.33 | 65 | 3750 | 97.3 | 98.6 |

We claim:

1. A process for preparing isophoronenitrile comprising adding HCN to isophorone, using, as a caytalyst, CAO having a BET surface area of >1.5 m²/g.

2. A process as claimed in claim 1, wherein the CaO used has a BET surface area of >2 m²/g.

3. A process as claimed in claim 1, wherein the CaO has a purity of >96%.

4. A process as claimed in claim 1, wherein the reaction is carried out at temperatures of from 100 to 200° C.

5. A process as claimed in claim 1, wherein the reaction is carried out at a pressure of ≧1 bar.

6. A process as claimed in claim 1, wherein the isophorone/HCN ratio is ≧1.

7. A process as claimed in claim 1, wherein isophorone and CaO are initially charged together and brought to the reaction temperature before the HCN is added.

8. A process as claimed in claim 1, wherein isophorone is initially charged alone and heated to the reaction temperature before CaO is added and then the HCN is added.

9. A process as claimed in claim 1, wherein a portion of the isophorone is initially charged and a mixture of isophorone and HCN is added.

10. A process as claimed in claim 1, wherein the concentration of the catalyst is from 2000 to 10000 ppm.

* * * * *